US008684736B2

(12) United States Patent
Kadobayashi

(10) Patent No.: US 8,684,736 B2
(45) Date of Patent: Apr. 1, 2014

(54) ARTIFICIAL TEETH

(75) Inventor: Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 320 days.

(21) Appl. No.: 12/461,101

(22) Filed: Jul. 31, 2009

(65) Prior Publication Data

US 2010/0035208 A1    Feb. 11, 2010

(30) Foreign Application Priority Data

Aug. 1, 2008 (JP) ................................ 2008-199290
Jul. 29, 2009 (JP) ................................ 2009-176724

(51) Int. Cl.
*A61C 13/10*    (2006.01)

(52) U.S. Cl.
USPC ........................................................ 433/191

(58) Field of Classification Search
USPC .................... 433/191, 192, 196, 197
See application file for complete search history.

(56) References Cited

U.S. PATENT DOCUMENTS

| 3,252,220 | A | 5/1966 | Goddard |
| 7,267,549 | B2 * | 9/2007 | Monkmeyer .................. 433/197 |
| 2004/0137404 | A1 * | 7/2004 | Koch et al. ...................... 433/81 |
| 2005/0095559 | A1 | 5/2005 | Monkmeyer |

FOREIGN PATENT DOCUMENTS

| JP | 2002-523134 | 3/2000 |
| JP | 2002-177301 | 6/2002 |
| JP | 2005-525841 | 9/2005 |

OTHER PUBLICATIONS

Notification of Reason for Refusal issued Feb. 9, 2010 (with English translation) in a Japanese application that is a foreign counterpart to the present application.

* cited by examiner

*Primary Examiner* — Sunil K Singh
(74) *Attorney, Agent, or Firm* — Wenderoth, Lind & Ponack, L.L.P.

(57) ABSTRACT

The invention enables to arrange teeth at appropriate positions depending on the oral cavity environment of each patient without requiring advanced techniques or experiments. In artificial molar teeth to be arranged on bases which are mounted in an oral cavity as a dental prosthetic appliance, an occlusal surfaces of the teeth are provided with side grooves extending toward a buccal side or lingual side, and intersecting portions (tops) of the side grooves with the outer circumference of the occlusal surface, and a contact point are formed on a plane parallel to the mesial distal direction. Or the teeth are configured such that the bottom ends of fossae on the occlusal surface and the contact point are formed on a plane parallel to the mesial distal direction. Alternatively, mutually parallel flat frictional contact portions are provided around cusps mutually contacting with the maxillary molar teeth and the mandibular molar teeth, respectively.

14 Claims, 6 Drawing Sheets

|  | DISTAL BUCCAL SIDE | MESIAL BUCCAL SIDE | DISTAL LINGUAL SIDE | MESIAL LINGUAL SIDE |
|---|---|---|---|---|
| MAXILLARY BUCCAL CUSP |  |  | THIRD FRICTIONAL PORTION | FIRST FRICTIONAL PORTION |
| MAXILLARY LINGUAL CUSP | SECOND FRICTIONAL PORTION | FOURTH FRICTIONAL PORTION | THIRD FRICTIONAL PORTION | FIRST FRICTIONAL PORTION |
| MANDIBULAR BUCCAL CUSP | FIRST FRICTIONAL PORTION | THIRD FRICTIONAL PORTION | FOURTH FRICTIONAL PORTION | SECOND FRICTIONAL PORTION |
| MANDIBULAR LINGUAL CUSP | FIRST FRICTIONAL PORTION | THIRD FRICTIONAL PORTION |  |  |

ARTIFICIAL TEETH

BACKGROUND OF THE INVENTION

I. Technical Field

The present invention relates to artificial molar teeth capable of easy arrangement when making a dental prosthetic appliance, and easy chewing at the time of mounting as dentures.

II. Description of Related Art

Arrangement of artificial molar teeth when making a dental prosthetic appliance demand advanced techniques and experiences. It has been particularly difficult to arrange opposed teeth in a proper position relation.

In dentures, in the presence of remaining teeth, artificial molar teeth may not be always arranged at specific positions, and the dentures must be tailored for each patient. It is hence impossible to array artificial molar teeth in a predetermined relation of upper and lower jaws, or array artificial molar teeth side by side. Conventionally, hence, after arranging, the artificial molar teeth are significantly ground, and the surface state is largely changed.

Japanese Patent Application Laid-Open No. 2002-177301 below discloses artificial molar teeth in which a lingual cusp, a buccal cusp, and a fossa are formed on the occlusal surface of maxillary molar teeth, and also a lingual cusp, a buccal cusp, and a fossa are formed on the occlusal surface of antagonist, i.e. opposed mandibular molar teeth. These artificial molar teeth are configured such that at a central occlusal position, the lingual cusp of the maxillary molar teeth occludes and contacts with the fossa of the mandibular antagonist, and the buccal cusp of the mandibular antagonist occludes and contacts with the fossa of the maxillary molar teeth.

In the artificial molar teeth disclosed in Japanese Patent Application Laid-Open No. 2002-177301, occlusal contact occurs in a total of 18 points, 9 points at the left and 9 points at the right. In other words, the number of occlusal contact points is smaller than in the full-balanced occlusion, and there is no occlusal contact with the inclined surface of the buccal cusp as in the full-balanced occlusion. Accordingly, when making dentures, arrangement on the wax alveolar ridge or occlusal adjustment by grinding or the like is easy. When the dentures are used, the dentures are stable without falling over. In mastication efficiency including grinding, biting and cutting of food, a satisfactory occlusion close to the full-balanced occlusion will be obtained. Moreover, changing to a lingualized occlusion can be easily conducted not only when making dentures but also when correcting the dentures.

However, in the artificial molar teeth disclosed in Japanese Patent Application Laid-Open No. 2002-177301, it is required to achieve occlusal contacts between the lingual cusp of maxillary molar teeth and the fossa of mandibular antagonist, and between the fossa of maxillary molar teeth and the buccal cusp of mandibular antagonist, respectively. Therefore, it has been extremely difficult to make dentures for each patient according to the complicated oral cavity environments of patients.

SUMMARY OF THE INVENTION

It is an object of the invention to provide artificial molar teeth that can be arranged at proper positions according to the oral cavity environment of each patient without requiring advanced techniques or experience.

In order to achieve the object, the first artificial molar teeth of the invention are configured such that in artificial molar teeth to be arranged on a base which is mounted in an oral cavity as a dental prosthetic appliance, in which an occlusal surface of the teeth is provided with a side groove extending toward a buccal side or lingual side in a state arranged on the base, and an intersecting portion of the side groove with the outer circumference of the occlusal surface, and a contact point with teeth arranged adjacently in a mesial distal direction are formed on a plane parallel to the mesial distal direction.

The artificial molar teeth are artificial molar teeth having two or more teeth to be arranged adjacently in the mesial distal direction on a base which is mounted in an oral cavity as a dental prosthetic appliance, and a cusp side embrasure being formed at a cusp side from a contact point with the outer circumference thereof, in which an occlusal surface of at least one tooth is provided with a side groove extending toward a buccal side or lingual side, and an intersecting portion of the side groove with the outer circumference of the occlusal surface and the contact point are formed on a plane parallel to the mesial distal direction.

The second artificial molar teeth of the invention are artificial molar teeth having two or more teeth to be arranged adjacently in the mesial distal direction on a base which is mounted in an oral cavity as a dental prosthetic appliance, and a cusp side embrasure being formed at a cusp side from a contact point with the outer circumference thereof, in which at least one tooth is configured such that the bottom end of a fossa on the occlusal surface of the tooth and the contact point are formed on a plane parallel to the mesial distal direction.

In these artificial molar teeth, the teeth have mutually occluding teeth on the opposed bases, and mutually parallel flat frictional contact portions are provided around the mutually contacting cusps of these teeth, respectively.

Further, the third artificial molar teeth of the invention are artificial molar teeth having maxillary molar teeth and mandibular molar teeth arranged on bases which are mounted on upper and lower jaws of an oral cavity as a dental prosthetic appliance, in which mutually parallel flat frictional contact portions are provided around the mutually contacting cusps of the maxillary molar teeth and mandibular molar teeth, respectively.

In this case, preferably, in each cusp of the maxillary molar teeth and mandibular molar teeth, the frictional contact portions of a distal buccal side are parallel to each other, and the frictional contact portions of a mesial buccal side are parallel to each other, and the frictional contact portions of a distal lingual side are parallel to each other, and the frictional contact portions of a mesial lingual side are parallel to each other.

Further preferably, the frictional contact portions of the mesial lingual side of the cusp of the maxillary molar teeth and the frictional contact portions of the distal buccal side of the cusp of the mandibular molar teeth are parallel to each other, the frictional contact portions of the distal buccal side of the cusp of the maxillary molar teeth and the frictional contact portions of the mesial lingual side of the cusp of the mandibular molar teeth are parallel to each other, the frictional contact portions of the distal lingual side of the cusp of the maxillary molar teeth and the frictional contact portions of the mesial buccal side of the cusp of the mandibular molar teeth are parallel to each other, and the frictional contact portions of the mesial buccal side of the cusp of the maxillary molar teeth and the frictional contact portions of the distal lingual side of the cusp of the mandibular molar teeth are parallel to each other.

In respective artificial molar teeth, the cusp tops of adjacent teeth are disposed so as to coincide with each other.

In the artificial molar teeth of the invention, only by disposing the intersecting portion of the side groove with the outer circumference of the occlusal surface, or the bottom end of the fossa at the occlusal surface and the contact point with the adjacently arranged teeth on a flat plane parallel to the mesial distal direction, the teeth can be positioned and arranged in the mesial distal direction without requiring any particular advanced techniques or experience. Since the mutually contacting teeth are provided with mutually parallel flat frictional contact portions, only by disposing them so as to contact surface to surface, the upper and lower teeth can be adjusted and arranged at specified positions without requiring any particular advanced techniques or experiences. The oral cavity environment of the patient varies significantly in individual patients, and the oral cavity, and the height and angle of an alveolar ridge are varied in the edentulous jaw. Even in such clinical cases, the artificial molar teeth can be arranged easily in a short time, and the oral cavity environment can be reproduced. Moreover, after mounting of the dental prosthetic appliance, the oral cavity is enhanced aesthetically.

If remaining teeth are present, it has been difficult to arrange the artificial molar teeth at specified positions, but the fitting positions of the upper and lower jaws can be adjusted easily. That is, various arrangement may be realized, for example, the positions of molar teeth may be changed, or to save the remaining premolar teeth, according to width and diameter, the molar tooth out of four teeth may be removed, or a first premolar tooth may be removed. Further, by the parallel frictional contact portion, mastication may be carried out easily, and a grinding function may be added to the cutting function.

BRIEF DESCRIPTION OF THE DRAWINGS

FIG. 2 (B) is a plan view showing a basic configuration of a maxillary premolar tooth.

FIG. 3 (B) is a plan view showing a basic configuration of a mandibular premolar tooth.

FIG. 8 is a table showing sites and types forming frictional contact portions.

DETAILED DESCRIPTION OF THE INVENTION

The embodiments of the invention are specifically described below with reference to drawings.

The invention is a technique for making artificial teeth as dental prosthetic appliances being dentures, and more particularly is a technique capable of applying for making of artificial molar teeth. The artificial molar teeth include a first molar tooth, a second molar tooth, a first premolar tooth, and a second premolar tooth, and two or more adjacent teeth of them are preferred to be combined, and in particular four pairs of teeth including upper and lower opposed teeth of opposed first molar teeth, opposed second molar teeth, opposed first premolar teeth, and opposed second premolar teeth are preferred.

Figure 1:
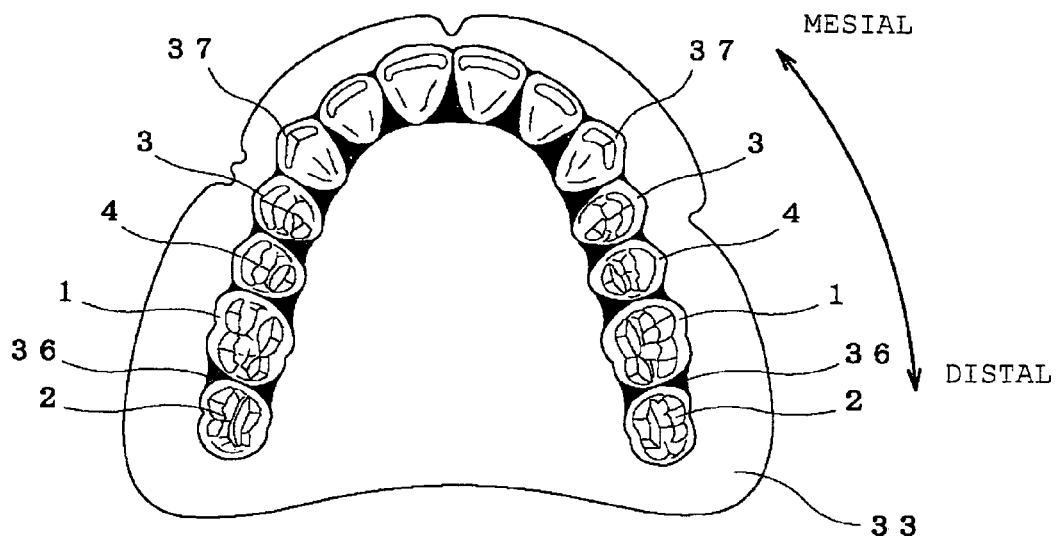
FIG. 1 is a plan view showing a basic configuration of artificial molar teeth disposed in an upper jaw and a lower jaw.
Figure 1:
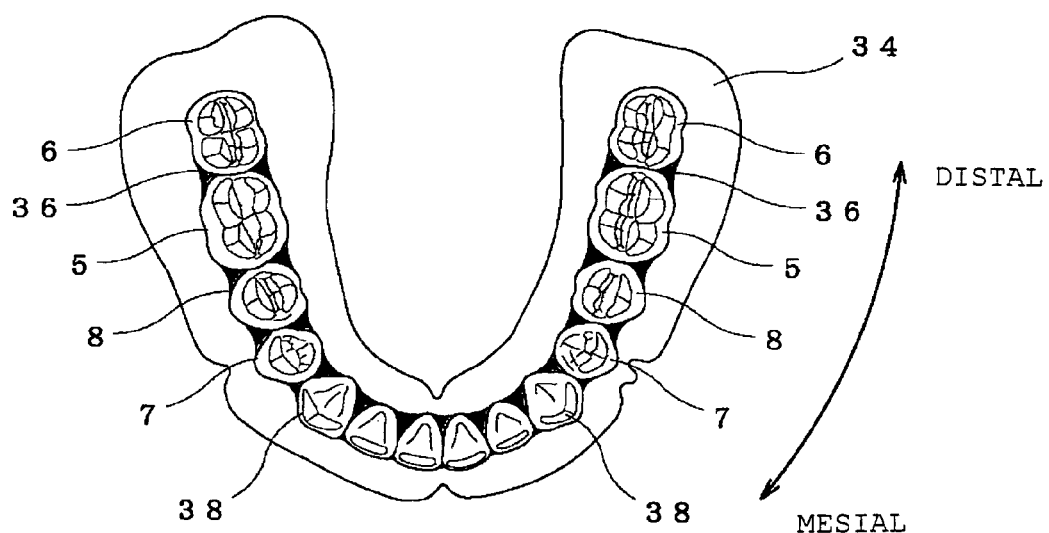
Figure 2:
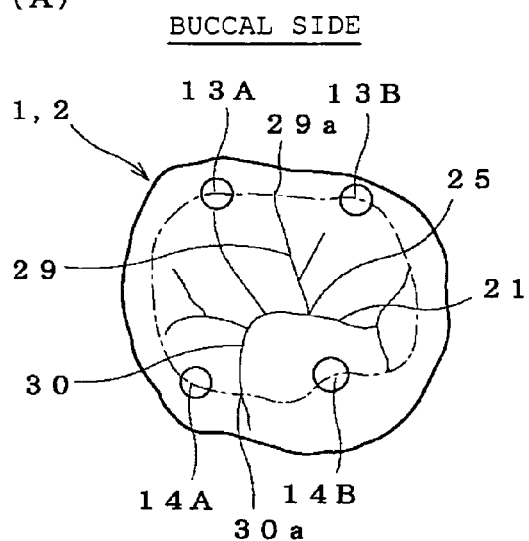
FIG. 2 (A) is a plan view showing a basic configuration of a maxillary molar tooth.
Figure 2:
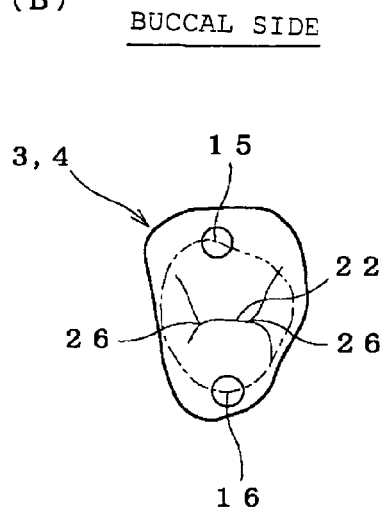
Figure 3:
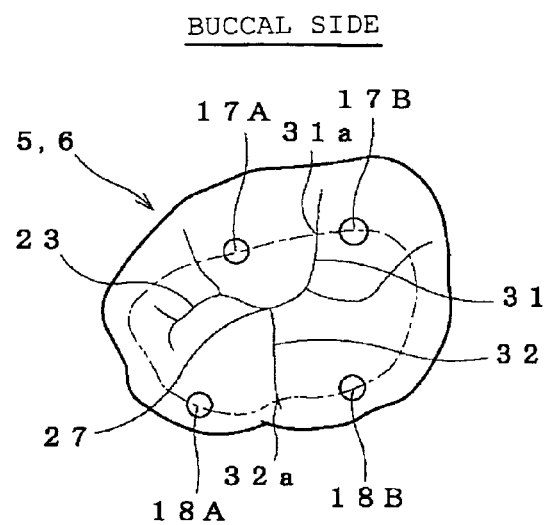
FIG. 3 (A) is a plan view showing a basic configuration of a mandibular molar tooth.
Figure 3:
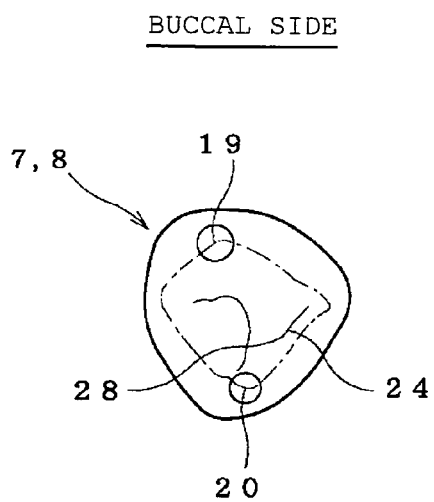

In the description below, a direction approaching to the anterior teeth is referred to as a mesial side, and a direction departing therefrom as a distal side. The inside of an oral cavity is referred to as a lingual side, and the outside as a buccal side. The occlusal surface side of a tooth is referred to as a cuspal side, and the root side of a tooth as a cervical side. FIG. 1 to FIGS. 3 (A) and (B) referred in the description below show basic configurations of artificial molar teeth, and the outer shape thereof or the like may be changed as desired.

FIG. 1 shows artificial teeth using the artificial molar teeth of the invention. The artificial molar teeth include a maxillary first molar tooth 1, a maxillary second molar tooth 2, a maxillary first premolar tooth 3, and a maxillary second premolar tooth 4 arranged in an upper jaw, and a mandibular first molar tooth 5, a mandibular second molar tooth 6, a mandibular first premolar tooth 7, and a mandibular second premolar tooth 8 arranged in an opposed lower jaw. The maxillary molar teeth 1 to 4 are opposed to the mandibular molar teeth 5 to 8, and the mandibular molar teeth 5 to 8 are opposed to the maxillary molar teeth 1 to 4. These teeth 1 to 8 are individually provided with first frictional contact portions 9, second frictional contact portions 10, third frictional contact portions 11, and fourth frictional contact portions 12, at cusps 13A, 13B to 16, 17A, 17B to 20 of mutually contacting teeth 1, 5 to 4, 8. The frictional contact portions 9 to 12 are flat planes extending parallel to each other.

More specifically, as shown in FIG. 2 (A), the maxillary molar teeth 1, 2 are provided with a pair of maxillary buccal cusps 13A, 13B at the buccal side, and a pair of maxillary lingual cusps 14A, 14B at the lingual side. Further, as shown in FIG. 2 (B), the maxillary premolar teeth 3, 4 are provided with a maxillary buccal cusp 15 at the buccal side, and a maxillary lingual cusp 16 at the lingual side. Moreover, as shown in FIG. 3 (A), the mandibular molar teeth 5, 6 are provided with, similarly to the maxillary molar teeth 1, 2, a pair of mandibular buccal cusps 17A, 17B at the buccal side, and a pair of mandibular lingual cusps 18A, 18B at the lingual side. Further, as shown in FIG. 3 (B), the mandibular premolar teeth 7, 8 are provided with a mandibular buccal cusp 19 at the buccal side, and a mandibular lingual cusp 20 at the lingual side. These cusps 13A, 13B to 20 have a shape in which a bulky tooth substance bulges in a tapered form. Besides, the mandibular first molar tooth 5 may be further provided with one cusp at the distal side. In the diagram, single-dot chain lines are ridges of upper and lower teeth 1 to 8, and the inside is the occlusal surface and the outside is the outer circumference of the teeth. The buccal side of the outer circumference is referred to as a buccal side surface, and the lingual side of the outer circumference as a lingual side surface. That is, the single-dot chain lines in the figure show the outer circumference of the occlusal surface.

The maxillary molar teeth 1, 2 are provided with grooves 21 extending toward the mesial distal direction between the maxillary buccal cusps 13A, 13B, and the maxillary lingual cusps 14A, 14B. The maxillary premolar teeth 3, 4 are provided with grooves 22 extending toward the mesial distal direction between the maxillary buccal cusp 15 and the maxillary lingual cusp 16. The mandibular molar teeth 5, 6 are provided with grooves 23 extending toward the mesial distal direction between the mandibular buccal cusps 17A, 17B, and the mandibular lingual cusps 18A, 18B. The mandibular premolar teeth 7, 8 are provided with grooves 24 extending toward the mesial distal direction between the mandibular buccal cusp 19 and the mandibular lingual cusp 20.

At a specified position (substantial center) on the grooves 21 of the maxillary molar teeth 1, 2, a fossa 25 of the greatest depth in the vertical direction in an arranged state is formed. At a specified position on the grooves 22 of the maxillary premolar teeth 3, 4, a fossa 26 is formed. At a specified position on the grooves 23 of the mandibular molar teeth 5, 6, a fossa 27 is formed. At a specified position on the grooves 23 of the mandibular premolar teeth 7, 8, a fossa 28 is formed.

On the occlusal surfaces of the maxillary molar teeth 1, 2, buccal side grooves 29 are formed between the maxillary buccal cusps 13A, 13B, and lingual side grooves 30 are formed between the maxillary lingual cusps 14A, 14B. Similarly, on the occlusal surfaces of the mandibular molar teeth 5, 6, buccal side grooves 31 are formed between the mandibular buccal cusps 17A, 17B, and lingual side grooves 32 are formed between the mandibular lingual cusps 18A, 18B. These buccal side grooves 29, 31 are large valleys formed at the buccal side by a pair of bulky buccal cusps 13A, 13B, 17A, 17B formed so as to bulge, and extend from the fossae 25, 27, or grooves 21, 23 toward the buccal side. Similarly, the lingual side grooves 30, 32 are large valleys formed at the lingual side by a pair of bulky lingual cusps 14A, 14B, 18A, 18B formed so as to bulge, and extend from the fossae 25, 27, or grooves 21, 23 toward the lingual side. These side grooves 29 to 32 are not formed in the upper and lower premolar teeth 3, 4, 7, 8. However, in the case of connected teeth formed by connecting a pair of premolar teeth, a groove such as a lingual side groove or buccal side groove is formed in the connection portion. Accordingly, when making the maxillary premolar teeth 3, 4 or mandibular premolar teeth 7, 8 as connected teeth, the grooves formed at the lingual side and the buccal side are handled similarly to the buccal side grooves 29, 31 and lingual side grooves 30, 32 of the molar teeth 1, 2, 5, 6.

Each of the teeth 1 to 8 having above configuration has an outer circumference formed in a curved surface except for the occlusal surface of the cuspal side. Of the outer circumference, excluding the distal side surface of the second molar teeth 2, 6, and excluding the buccal side surface and lingual side surface, the remaining surfaces are the surfaces opposite to the adjacent teeth 1 to 4, 5 to 8. When the maxillary molar teeth 1 to 4 are arranged on a maxillary base 33, and the mandibular molar teeth 5 to 8 are arranged on a mandibular base 34, the adjacent teeth 1 to 4, and 5 to 8 contact with each other at one point on the outer circumference. In other words, the teeth 1 to 8 are formed in a curved shape such that one point on the outer circumference may be a contact point 35, and the teeth are arranged such that these contact points 35 may contact with each other. As shown by shading in FIG. 1, an embrasure 36 formed of hand drum-shaped gaps (spaces) is formed among the adjacent teeth 1 to 4, and 5 to 8. This embrasure 36 is divided into a cuspal side embrasure 36a at the cuspal side from the contact point 35, and a cervical side embrasure 36b at the cervical side from the contact point 35.

Figure 4:
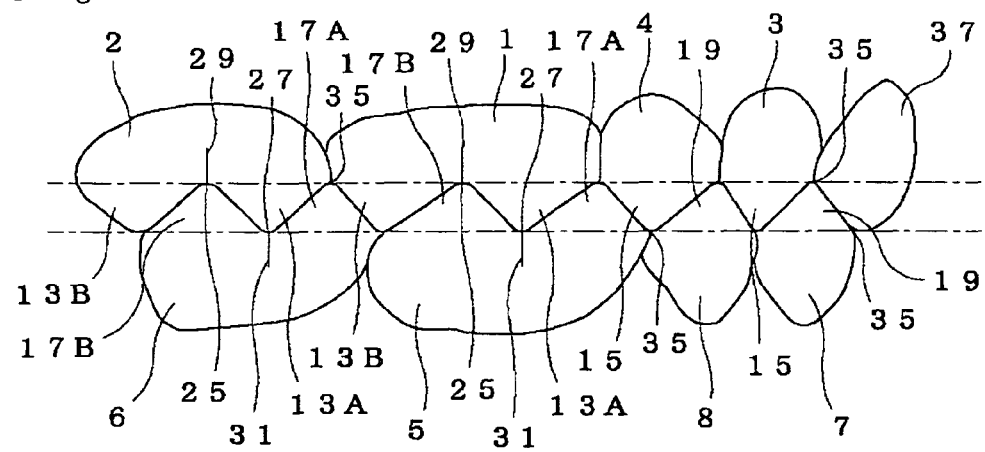
FIG. 4 is a buccal side view showing a state of the maxillary molar teeth and the mandibular molar teeth of the invention arranged and placed in the upper and lower positions, respectively.

Of these teeth 1 to 8, the maxillary and mandibular molar teeth 1, 2, 5, 6 are configured such that the depth of the cuspal side embrasure 36a of the adjacent teeth 4, 1, 8, 5, and the depth of one or more of the buccal side grooves 29, 31 and the lingual side grooves 30, 32 may be nearly the same. In particular, the depth of the cuspal side embrasure 36a of the adjacent teeth 4, 1, 8, 5 and the depth of the buccal side grooves 29, 31 and the lingual side grooves 30, 32 may be preferably all the same. FIG. 4 is a view seen from the buccal side in which the molar teeth 1 to 4, and 5 to 8 of the invention are arranged on maxillary and mandibular bases 37, 38, respectively, and arranged in the upper and lower positions. FIG. 4 is also a view in which the buccal sides of the right side maxillary and mandibular molar teeth are aligned so as not to cover, and the maxillary and mandibular molar teeth 1 to 4, and 5 to 8 are stacked such that the cusp tops thereof may be visible.

As shown in FIG. 4, in the molar teeth 1, 2, 5, 6 of the embodiment, the buccal side grooves 29, 31 and lingual side grooves 30, 32 provided on the occlusal surface are extended to the buccal side surface and the lingual side surface. These buccal side grooves 29, 31 and lingual side grooves 30, 32 are provided such that the portions intersecting with the outer circumference of the occlusal surface, that is, cuspal side tops 29a to 32a may correspond to the contact point 35 contacting with the adjacent teeth 4, 1, 8, 5 in the mesial distal direction. That is, the tops 29a to 32a of the side grooves 29 to 32 and the contact point 35 of the outer circumference are located on a plane parallel to the mesial distal direction (on the single-dot chain line in the drawing). In other words, the outer circumferences of the molar teeth 1, 2, 5, 6 are formed in a curved shape such that the root portions of the cusps 13A, 13B, 14A, 14B, 17A, 17B, 18A, 18B formed so as to bulge, and the contact point 35 with the adjacently arranged teeth 4, 1, 8, 5 may be located on a plane parallel to the mesial distal direction. As a result, the depth of the cuspal side embrasure 36a of the adjacent teeth 4, 1, 8, 5 and the depth of the buccal side grooves 29, 31 and the lingual side grooves 30, 32 may be nearly all the same.

Also, the molar teeth 1, 2, 5, 6 of the embodiment are formed such that the depth of the cuspal side embrasure 36a, and the depth to the bottom ends of the fossae 25, 27 may be nearly the same. However, the depth of the cuspal side embrasure 36a, and the depths of the fossae 25, 27 may not need to be strictly the same, but are preferred to be nearly equal to each other. Moreover, even if the lower jaw is moved back and forth by one cusp move (motion), it is preferred that the cusps 13A, 13B to 16, 17A, 17B to 20 may maintain the same relation. As a result, if the cusps 13A, 13B to 16, 17A, 17B to 20 are fitted by shifting by each one, it is desired to maintain the same motion as in the central occlusion.

Figure 5:
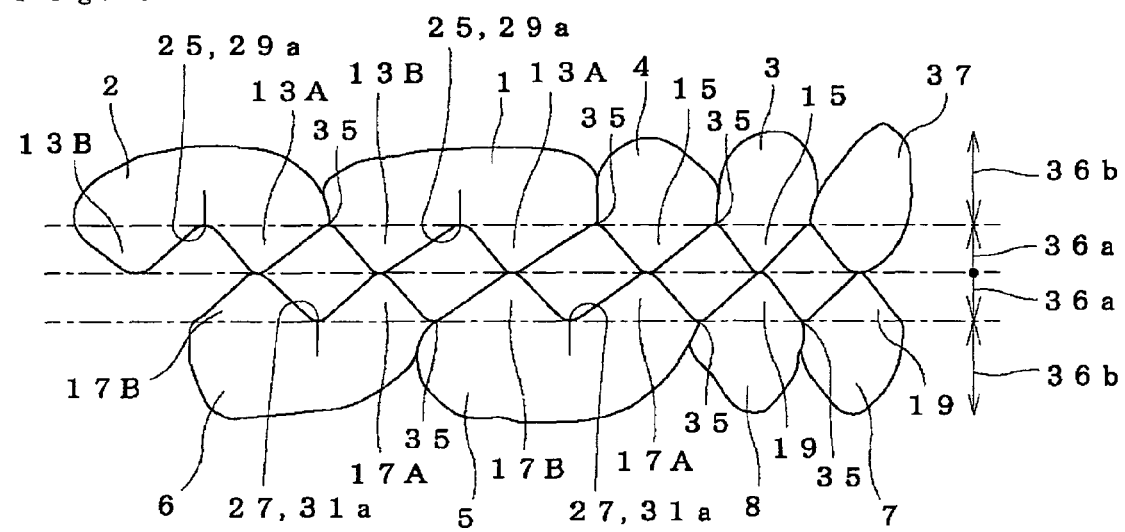
FIG. 5 is a buccal side view showing a joined state of the cusp tops of artificial molar teeth.

In order to achieve such configuration, in the embodiment, the bottom ends of the fossae 25, 27 of the molar teeth 1, 2, 5, 6 and the contact point 35 of the outer circumference are disposed so as to correspond in the mesial distal direction. That is, the bottom ends of the fossae 25, 27 of the molar teeth 1, 2, 5, 6 and the contact point 35 of the outer circumference is provided so as to be located on a plane parallel to the mesial distal direction. Further, as shown in FIG. 5, the dimensional relation of the cusps 13A, 13B to 20, and the fossae 25 to 28 in the mesial distal direction is kept constant so that the maxillary molar teeth 1 to 4 and the mandibular molar teeth 5 to 8 can be fitted correctly. Moreover, the shape of the cuspal side embrasure 36a of the adjacent teeth 1 to 4, 5 to 8 and the shapes of the lingual side grooves 30, 32 and the buccal side grooves 29, 31 are configured to be a nearly identical form. In other words, the space shape formed among the adjacent cusps 13A, 13B to 16, and the shape of the opposed cusps 17A, 17B to 20 are configured to be a nearly identical form. In FIG. 5, since the mesial side is curved to the inner side, the shapes are not identical, but the actual shapes are nearly the same.

Figure 6:
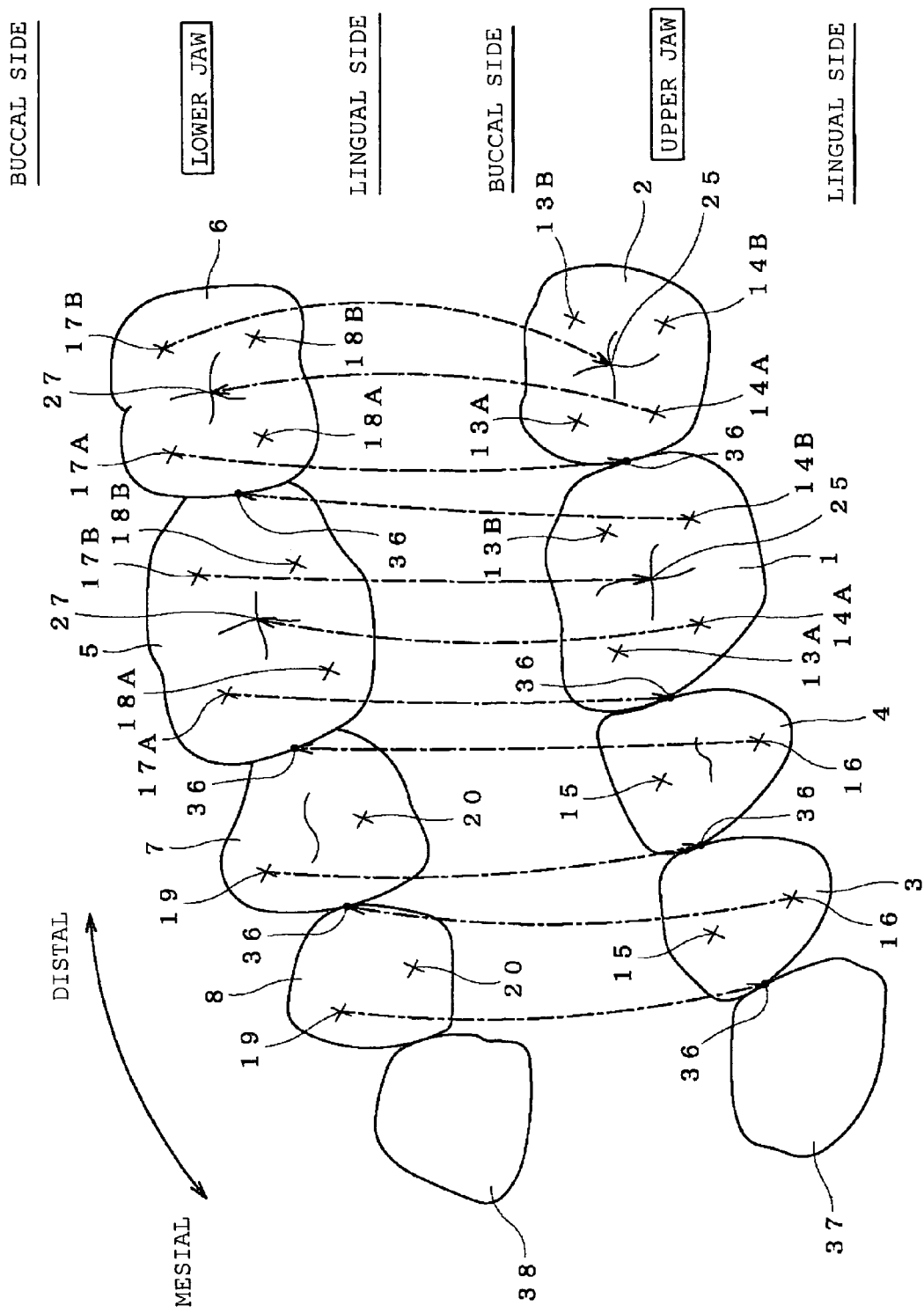
FIG. 6 is a conceptual diagram showing a relation of cusps, fossae and cusp side embrasures of an occlusal surface as seen from the maxillary direction in maxillary molar teeth and mandibular molar teeth arranged and placed in the upper and lower positions.

FIG. 6 shows, showing the relation of the cusps 13A, 13B to 20 and the fossae 25 to 28 of the occlusal surface, as seen from the maxillary direction, of the maxillary molar teeth 1 to 4 and the mandibular molar teeth 5 to 8 of the embodiment arranged respectively on the bases 37, 38, and the cuspal side embrasure 36a. The upper side is a view of the lower jaw seen from the maxillary direction, and the lower side is a view of the upper jaw seen from the maxillary direction similarly to the case of the lower jaw. However, when the upper jaw is seen from the maxillary direction, the state of occlusion is not found, and hence the state of occlusion as seen from above is shown in order to indicate the state of occlusion.

As shown in FIG. 6, the mandibular buccal cusp 17B of the mandibular second molar tooth 6 is fitted to the fossa 25 of the maxillary second molar tooth 2. The mandibular buccal cusp 17A of the mandibular second molar tooth 6 is fitted between the maxillary second molar tooth 2 and the maxillary first molar tooth 1, that is, in the cuspal side embrasure 36a. The mandibular buccal cusp 17B of the mandibular first molar tooth 5 is fitted to the fossa 25 of the maxillary first molar tooth 1. The mandibular buccal cusp 17A of the mandibular first molar tooth 5 is fitted to the cuspal side embrasure 36a between the maxillary first molar tooth 1 and the maxillary second premolar tooth 4. The mandibular buccal cusp 19 of the mandibular second premolar tooth 8 is fitted to the cuspal side embrasure 36a between the maxillary second premolar tooth 4 and the maxillary first premolar tooth 3. The mandibular buccal cusp 19 of the mandibular first premolar tooth 7 is fitted to the cuspal side embrasure 36a between the maxillary first premolar tooth 3 and the maxillary canine tooth 37. The maxillary lingual cusp 14A of the maxillary second molar tooth 2 is fitted to the fossa 27 of the mandibular second molar tooth 6. The maxillary lingual cusp 14B of the maxillary first molar tooth 1 is fitted to the cuspal side embrasure 36a between the mandibular second molar tooth 6 and the mandibular first molar tooth 5. The maxillary lingual cusp 14A of the maxillary first molar tooth 1 is fitted to the fossa 27 of the mandibular first molar tooth 5. The maxillary lingual cusp 16 of the maxillary second premolar tooth 4 is fitted to the cuspal side embrasure 36a between the mandibular first molar tooth 5 and the mandibular second premolar tooth 8. The maxillary lingual cusp 16 of the maxillary first premolar tooth 3 is fitted to the cuspal side embrasure 36a between the mandibular second premolar tooth 8 and mandibular first premolar tooth 7. Meanwhile, the maxillary lingual cusp 14B of the maxillary second molar tooth 2 is not fitted due to the relation of the number of cusps.

However, these cusp tops to be occluded with the cuspal side embrasure 36a may be configured to be occluded to the nearby fossa. Clinically, since an adjacent tooth may not be necessarily a prosthetic tooth, it is more preferred to be occluded with the fossa or minor fossa of identical antagonist than to be occluded with the cuspal side embrasure 36a made simultaneously with the adjacent tooth. The identical antagonist refer to, for example, the maxillary first molar tooth 1 with the mandibular first molar tooth 5, or the maxillary second molar tooth 2 with the mandibular second molar tooth 6.

In this manner, the cusps 13A, 13B to 20, the fossae 25 to 28, and the cuspal side embrasure 36a of the teeth 1 to 8 are formed in a specific relation, causing, as shown in FIG. 5, the position relation of the maxillary cusp tops and the position relation of the mandibular cusp tops to coincide with each other. Further, each inclination angle to antagonists 1 to 4, 5 to 8 of the cusps 13A, 13B to 16, 17A, 17B, and 20 is identical, and the relation between cusps of the teeth 1 to 4 arranged on the upper jaw coincides with the relation between cusps of the teeth 5 to 8 arranged on the lower jaw. This configuration is preferred because it is easy to confirm the state of arrangement when arranging the cusps.

The maxillary and mandibular molar teeth 1 to 4, 5 to 8 arranged in such a specific relation are moved in the lateral motion, forward motion, and backward motion of the lower jaw in a state where the cusps 13A, 13B to 16, 17A, 17B, and 20 are fitted with the fossae 25 to 28, and the cuspal side embrasure 36a. Frictional contact portions 9 to 12 are provided in the rubbing parts in those motions. These frictional contact portions 9 to 12 are provided as flat shapes extending parallel to each other, on one or more slopes at the mesial, distal, lingual, and buccal side in the mutually contacting cusps 13A, 13B to 16, 17A, 17B to 20. However, even in the frictional situation, nearly parallel state is not maintained between the left jaw and the right jaw. It is hence preferred to form frictional contact portions 9 to 12 in flat shapes nearly parallel to each other in four or more cusps. It is more preferred to form the frictional contact portions 9 to 12 in flat shapes nearly parallel to each other in six cusps.

That is, in the forward motion of the jaw, the distal side slopes of the maxillary lingual cusps 14A, 14B, 16 contact with the mesial side slopes of the mandibular lingual cusps 18A, 18B, 20 to be rubbed with each other. In the lateral motion of the lower jaw at the balanced side, the lingual side slopes of the maxillary buccal cusps 13A, 13B, 15 contact with the buccal side slopes of the mandibular buccal cusps 17A, 17B, 19 to be rubbed with each other. In the lateral motion at the balanced side, moreover, the lingual side slopes of the maxillary lingual cusps 14A, 14B, 16 contact with the buccal side slopes of the mandibular lingual cusps 18A, 18B, 20 to be rubbed with each other. In the lateral motion, at the working side, the buccal side slopes of the maxillary lingual cusps 14A, 14B, 16 contact with the lingual side slopes of the mandibular buccal cusps 17A, 17B, 19 to be rubbed with each other.

Figure 7:
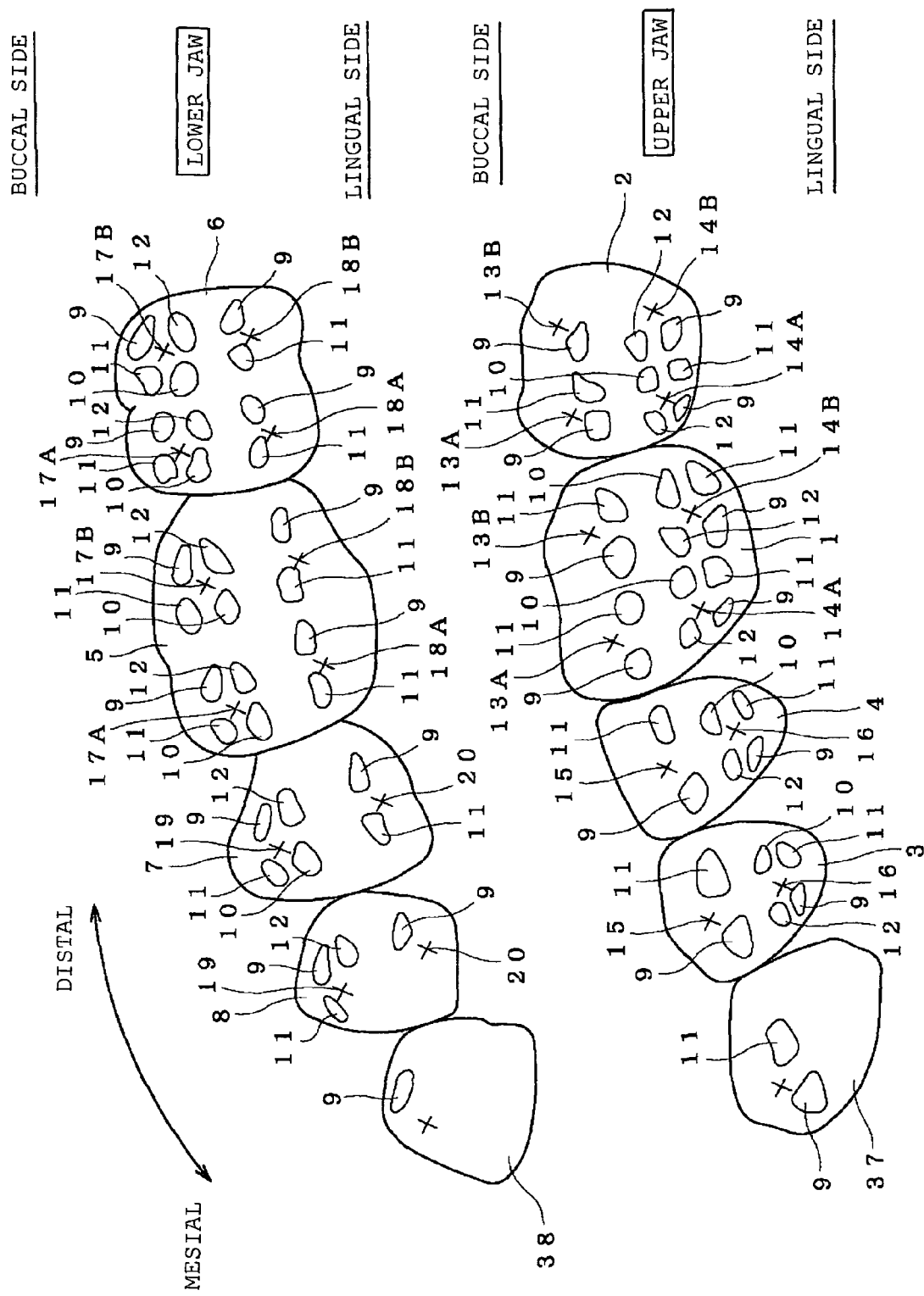
FIG. 7 is a conceptual diagram showing flat frictional contact portions formed on each cusp.

According to the embodiment, as shown in FIG. 7 and FIG. 8, at each of the cusps 13A, 13B to 16 of the maxillary molar teeth 1 to 4, the first to fourth frictional contact portions 9 to 12 are provided respectively at the distal buccal side, mesial buccal side, distal lingual side, and mesial lingual side. Similarly, at each of the cusps 17A, 17B to 20 of the mandibular molar teeth 5 to 8, the first to fourth frictional contact portions 9 to 12 are provided respectively at the distal buccal side, mesial buccal side, distal lingual side, and mesial lingual side. In an arranged state, it is configured such that all the first frictional contact portions 9 are in parallel, all the second frictional contact portions 10 are in parallel, all the third frictional contact portions 11 are in parallel, and all the fourth frictional contact portions 12 are in parallel. That is, the cusps 13A, 13B to 20 have four sides, and these sides are located in the mesial buccal side direction, mesial lingual side direction, distal buccal side direction, and distal lingual side direction. The sides in common directions of the cusps 13A, 13B to 20 form nearly parallel surfaces. For example, nearly parallel surfaces are formed on the sides in each mesial buccal side direction of each cusp of prosthetic teeth. On other sides of other cusps, similarly, common parallel surfaces are formed. Corresponding to the surfaces, the antagonist form common and nearly parallel surfaces.

Specifically, since the buccal cusps 13A, 13B, 15 of the maxillary molar teeth 1 to 4 do not rub against the other cusps on the buccal side slopes, any frictional contact portions are not provided. The buccal cusps 13A, 13B, 15 of the maxillary molar teeth 1 to 4 rub against the buccal cusps 17A, 17B to 20 of the mandibular molar teeth 5 to 8, on the lingual side slopes. Hence, the first frictional contact portions 9 are provided on the mesial lingual side slopes of the maxillary buccal cusps 13A, 13B, 15, and the first frictional contact portions 9 are provided also on the distal buccal side slopes of the corresponding mandibular buccal cusps 17A, 17B, 19. Further, the third frictional contact portions 11 are provided on the distal lingual side slopes of the maxillary buccal cusps 13A, 13B, 15, and the third frictional contact portions 11 are provided also on the mesial buccal side slopes of the corresponding mandibular buccal cusps 17A, 17B, 19.

The lingual cusps 14A, 14B, 16 of the maxillary molar teeth 1 to 4 rub against the buccal cusps 17A, 17B, 19 of the mandibular molar teeth 5 to 8 on the buccal side slopes, and rub against the lingual cusps 18A, 18B, 20 of the mandibular molar teeth 5 to 8 on the lingual side slopes. Accordingly, the second frictional contact portions 10 are provided on the distal buccal side slopes of the maxillary lingual cusps 14A, 14B, 16, and the second frictional contact portions 10 are provided also on the mesial lingual side slopes of the corresponding mandibular buccal cusps 17A, 17B, 19. Further, the fourth frictional contact portions 12 are provided on the mesial buccal side slopes of the maxillary lingual cusps 14A, 14B, 16, and the fourth frictional contact portions 12 are provided also on the distal lingual side slopes of the corresponding mandibular buccal cusps 17A, 17B, 19. Moreover, the first frictional contact portions 9 are provided on the mesial lingual side slopes of the maxillary lingual cusps 14A, 14B, 16, and the first frictional contact portions 9 are provided also on the distal buccal side slopes of the corresponding mandibular lingual cusps 18A, 18B, 20. Further, the third frictional contact portions 11 are provided on the distal lingual side slopes of the maxillary lingual cusps 14A, 14B, 16, and the third frictional contact portions 11 are provided also on the mesial buccal side slopes of the corresponding mandibular lingual cusps 18A, 18B, 20.

However, in the maxillary second molar tooth 2 out of the maxillary molar teeth 1 to 4, since the distal side slopes of the maxillary buccal cusp 13B and the maxillary lingual cusp 14B do not rub against other cusps, any frictional contact portions are not provided. In the mandibular molar teeth 5 to 8, since the lingual side slopes of the lingual cusps 18A, 18B, 20 do not rub against other cusps, any frictional contact portions are not provided. In the mandibular first premolar tooth 7 of the mandibular molar teeth 5 to 8, since the mesial side slope of the mandibular lingual cusp 20 does not rub against other cusps, any frictional contact portions are not provided. These slopes not forming frictional contact portions are preferred to be formed in a curved bulged portion so as to improve a touch with the tongue. In the embodiment, the corresponding third frictional contact portion 11 is provided in the maxillary canine tooth 37 rubbing against the mandibular buccal cusp 19 of the mandibular first premolar tooth 7. In the maxillary canine tooth 37 of the embodiment, the first frictional contact portion 9 is further provided at the distal side, and the corresponding first frictional contact portion 9 is provided also in the rubbing mandibular canine tooth 38.

When these teeth 1 to 8 are arranged on bases 37, 38, for example, the maxillary first premolar tooth 3 is arranged at the distal side of the maxillary canine tooth 37. At this time, the maxillary canine tooth 37 may be either a prosthetic or remaining tooth. In the case of the remaining tooth, the maxillary base 33 is disposed as an artificial gum in the mesial distal direction of the remaining gum. In the maxillary first premolar tooth 3, the contact point 35 is brought into contact with the adjacent maxillary canine tooth 37 such that the tops of the cusps 15, 16 may coincide with the top of the maxillary canine tooth 37 in the mesial distal direction (the height may be matched in the cervical cusp direction).

Next, the maxillary second premolar tooth 4 is arranged on the maxillary base 33. At this time, in the maxillary second premolar tooth 4, the contact point 35 is brought into contact with the adjacent maxillary first premolar tooth 3 such that the tops of the cusps 15, 16 may coincide with the top of the maxillary first premolar tooth 3 in the mesial distal direction. The arrangement is determined such that this contact point 35 coincides with the contact point 35 of the adjacently arranged maxillary first premolar tooth 3 and maxillary canine tooth 37 in the mesial distal direction.

Next, the maxillary first molar tooth 1 is arranged on the maxillary base 33. At this time, the maxillary first molar tooth 1 is arranged such that any one of the top 29a of the buccal side groove 29, the top 30a of the lingual side groove 30, and the fossa 25, the mesial side contact point 35, and the contact point 35 of the adjacently arranged maxillary premolar teeth 3, 4 coincide with one another in the mesial distal direction.

Next, the maxillary second molar tooth 2 is arranged on the maxillary base 33. At this time, the maxillary second molar tooth 2 is arranged such that anyone of the top 29a of the buccal side groove 29, the top 30a of the lingual side groove 30, and the fossa 25, the mesial side contact point 35, and any one of the top 29a of the buccal side groove 29, the top 30a of the lingual side groove 30, and the fossa 25 of the adjacently arranged maxillary first molar tooth 1 coincide with one another in the mesial distal direction.

Thus, since the maxillary molar teeth 1, 2 are made such that the top 29a of the buccal side groove 29, the top 30a of the lingual side groove 30, and the bottom end of the fossa 25, and the contact point 35 of the adjacent teeth 1, 4 are positioned on a plane parallel to the mesial distal direction, and the operability is extremely good when arranging adjacently in the mesial distal direction. Accordingly, without requiring advanced techniques and experiences, the teeth can be arranged at proper positions depending on the oral cavity environment of each patient. When the maxillary molar teeth 1 to 4 are arranged properly in this way, the tops of the cusps 13A, 13B to 16 coincide in the mesial distal direction, and are positioned straightly. Of course, when the mandibular molar teeth 5 to 8 are previously arranged, since the mandibular molar teeth 5 to 8 have similar configurations, the same action and effects will be obtained.

Next, the mandibular first premolar tooth 7 is arranged on the mandibular base 34. At this time, similarly to the maxillary first premolar tooth 3, the contact point 35 is brought into contact with the adjacent mandibular canine tooth 38 such that the tops of the cusps 19, 20 coincide with the top of the mandibular canine tooth 38 in the mesial distal direction. Moreover, the previously arranged maxillary molar teeth 1 to 4 are occluded, and the surface contact is adjusted such that the third frictional contact portion 11 and first frictional contact portion 9 of the mandibular buccal cusp 19 of the mandibular first premolar tooth 7 contact with the third frictional contact portion 11 of the maxillary canine tooth 37 and the first frictional contact portion 9 of the maxillary first premolar tooth 3. This adjustment operation includes the arrangement adjustment of the maxillary first premolar tooth 3.

Next, the mandibular second premolar tooth 8 is arranged on the mandibular base 34. At this time, the contact point 35 is brought into contact with the adjacent mandibular first premolar tooth 7 such that the tops of the cusps 19, 20 coincide with the top of the mandibular first premolar tooth 7 in the mesial distal direction. The teeth are arranged such that the contact point 35 coincides with the contact point 35 of adjacently arranged mandibular first premolar tooth 7 and the maxillary canine tooth 37 in the mesial distal direction. The previously arranged maxillary molar teeth 1 to 4 are occluded, and the surface contact is adjusted such that the third frictional contact portion 11 and first frictional contact portion 9 of the mandibular buccal cusp 19 of the mandibular second premolar tooth 8 contact with the third frictional contact portion 11 of the maxillary first premolar tooth 3 and the first frictional contact portion 9 of the maxillary second premolar tooth 4.

Next, the mandibular first molar tooth 5 is arranged on the mandibular base 34. At this time, the mandibular first molar tooth 5 is arranged such that any one of the top 31a of the buccal side groove 31, the top 32a of the lingual side groove 33, and the fossa 27, the mesial side contact point 35, and the contact point 35 of the adjacently arranged maxillary premolar teeth 7, 8 coincide with one another in the mesial distal direction. The previously arranged maxillary molar teeth 1 to 4 are occluded, and the surface contact is adjusted such that the third frictional contact portion 11 of the mandibular buccal cusp 17A of the mandibular first molar tooth 5 contacts with the third frictional contact portion 11 of the maxillary second premolar tooth 4, that the first frictional contact portion 9 of the mandibular buccal cusp 17A of the mandibular first molar tooth 5 contacts with the first frictional contact portion 9 of the maxillary buccal cusp 13A of the maxillary first molar tooth 1, that the third frictional contact portion 11 of the mandibular buccal cusp 17B of the mandibular first molar tooth 5 contacts with the third frictional contact portion 11 of the maxillary buccal cusp 13A of the maxillary first molar tooth 1, and that the first frictional contact portion 9 of the mandibular buccal cusp 17B of the mandibular first molar tooth 5 contacts with the first frictional contact portion 9 of the maxillary buccal cusp 13B of the maxillary first molar tooth 1.

Finally, the mandibular second molar tooth 6 is arranged on the mandibular base 34. At this time, the mandibular second molar tooth 6 is arranged such that any one of the top 31a of the buccal side groove 31, the top 32a of the lingual side groove 33, and the fossa 27, the mesial side contact point 35, and any one of the top 31a of the buccal side groove 31, the top 32a of the lingual side groove 33, and the fossa 27 coincide with one another in the mesial distal direction. The previously arranged maxillary molar teeth 1 to 4 are occluded, and the surface contact is adjusted such that the third frictional contact portion 11 of the mandibular buccal cusp 17A of the mandibular second molar tooth 6 contacts with the third frictional contact portion 11 of the mandibular buccal cusp 17B of the mandibular second molar tooth 6, that the first frictional contact portion 9 of the mandibular buccal cusp 17A of the mandibular second molar tooth 6 contacts with the first frictional contact portion 9 of the maxillary buccal cusp 13A of the maxillary second molar tooth 2, that the third frictional contact portion 11 of the mandibular buccal cusp 17B of the mandibular second molar tooth 6 contacts with the third frictional contact portion 11 of the maxillary buccal cusp 13A of the maxillary second molar tooth 2, and that the first frictional contact portion 9 of the mandibular buccal cusp 17B of the mandibular second molar tooth 6 contacts with the first frictional contact portion 9 of the maxillary buccal cusp 13B of the maxillary second molar tooth 2.

In this way, the opposed mandibular molar teeth 5 to 8, like the maxillary molar teeth 1 to 4, can be arranged at appropriate positions according to the oral cavity environment of each patient without requiring advanced techniques or experiences. Moreover, in the embodiment, since the frictional contact portions 9 to 12 extending parallel to each other are provided in the maxillary molar teeth 1 to 4 and the mandibular molar teeth 5 to 8, the upper and lower positional relation can be easily adjusted and the teeth can be arranged. Of course, the same action and effects are obtained when the mandibular molar teeth 5 to 8 are arranged first and the maxillary molar teeth 1 to 4 are arranged later.

A method of arranging the teeth 1 to 8 may be changed variously. For example, after arranging the maxillary molar teeth 1 to 4, instead of arranging the mandibular molar teeth 5 to 8, the first premolar tooth 3 or 7 of either upper jaw or lower jaw is arranged first, and then the first premolar tooth 7 or 3 of the other jaw is arranged while being adjusted. Consequently, the second premolar teeth 4, 8, the first molar teeth 1, 5, and the second molar teeth 2, 7 are sequentially adjusted and arranged in the mesial distal direction. In this manner, similarly as described above, it is easy to arrange in the mesial distal direction, and the maxillary and mandibular molar teeth 1 to 4, 5 to 8 can be easily adjusted at corrected positions.

As described herein, in the artificial molar teeth 1 to 8 of the embodiment, when making artificial molar teeth by adjusting to the oral cavity environment of a patient, the maxillary and mandibular molar teeth 1 to 4, 5 to 8 can be arranged at specified positions without requiring advanced techniques or experiences. That is, the oral cavity environment of the patient varies significantly in individual patients, and the oral cavity, and the height and angle of an alveolar ridge are varied in the edentulous jaw, and even in such clinical cases, the artificial molar teeth can be arranged easily in a short time, and the oral cavity environment can be reproduced. Further, if remaining teeth are present, it has been difficult to arrange the artificial molar teeth 1 to 8 at specified positions, but the fitting positions of the upper and lower jaws can be adjusted easily. That is, various arrangement are possible, for example, the positions of the molar teeth 1, 2, 5, 6 may be changed, or to save the remaining premolar teeth, according to width and diameter, the molar teeth 1, 2, 5, 6 out of four molar teeth may be removed, or the first premolar tooth 3 or 7 may be removed. Moreover, depending on the relation of depth and position of the cusps 13A, 13B, 14A, 14B, 17A, 17B, 18A, 18B, the fossae 25, 27, and the embrasure 36a of each of the teeth 1 to 8, and owing to the parallel frictional contact portions 9 to 12, mastication may be carried out easily, and grinding function may be added to the cutting function. Moreover, after mounting of the dental prosthetic appliance, the oral cavity is enhanced aesthetically.

The artificial molar teeth of the invention is not limited to the configurations shown in the embodiment, but may be modified variously.

For example, in the embodiment, it was figured such that the both tops of the buccal side grooves 29, 31 and the lingual side grooves 30, 32 are formed on a plane parallel to the contact point 35 and the mesial distal direction, but either one may be formed on a plane parallel to the mesial distal direction. It was figured such that the both tops of the side grooves 29 to 32, and the bottom ends of the fossae 25, 27 are formed on a plane parallel to the contact point 35 and the mesial distal direction, but either one may be formed on a plane parallel to the mesial distal direction. That is, any one of the tops of the buccal side grooves 29, 31, the tops of the lingual side grooves 30, 32, and the bottom ends of the fossae 25, 27, and the contact point 35 may be formed on a plane parallel to the mesial distal direction.

What is claimed is:

1. Artificial molar teeth to be arranged on a base which is mounted in an oral cavity as a dental prosthetic appliance, said artificial molar teeth comprising:
a plurality of artificial molar teeth, at least one artificial molar tooth of said plurality of artificial molar teeth including an occlusal surface having cusps and a side groove, said occlusal surface further having an outer circumference defined by a ridge line extending over said cusps and crossing said side groove, said side groove extending toward a buccal side or lingual side when said plurality of artificial molar teeth are arranged on the base, wherein said side groove extends from a fossa to a highest point of said side groove, wherein said side groove includes an intersecting point that intersects with said outer circumference of the occlusal surface, said intersecting point being located at the highest point of said side groove on said occlusal surface, and wherein said at least one artificial molar tooth includes a contact point that contacts an adjacent tooth that is arranged adjacently in a mesial distal direction, said intersecting point and said contact point being formed on a plane parallel to the mesial distal direction.

2. Artificial molar teeth comprising:

two or more teeth configured to be arranged adjacently in a mesial distal direction on a base, which is configured to be mounted in an oral cavity as a dental prosthetic appliance, said two or more teeth contacting each other at a contact point therebetween when arranged adjacently, wherein a cusp side embrasure is formed at a cusp side of each tooth in said two or more teeth, each said cusp side having an outer circumferential area, and said cusp side embrasure is formed from said contact point and includes said outer circumferential area of each said cusp side, wherein an occlusal surface of at least one tooth includes cusps and a side groove, said occlusal surface further having an outer circumference defined by a ridge line extending over said cusps and crossing said side groove, said side groove extending toward a buccal side or lingual side, wherein said side groove extends from a fossa to a highest point of said side groove, wherein an intersecting point of said side groove intersects with said outer circumference of said occlusal surface, said intersecting point being located at the highest point of said side groove on said occlusal surface, wherein said intersecting point and said contact point are formed on a plane parallel to the mesial distal direction, and wherein said circumferential area is an area outside of said outer circumference of said occlusal surface.

3. The artificial molar teeth according to claim 1, wherein said plurality of artificial molar teeth includes mutually occluding teeth on opposed bases, and mutually parallel flat frictional contact portions are provided around mutually contacting cusps of said plurality of artificial molar teeth.

4. The artificial molar teeth according to claim 3, wherein said plurality of artificial molar teeth includes maxillary molar teeth and mandibular molar teeth, and in each cusp of said cusps of said maxillary molar teeth and said mandibular molar teeth, frictional contact portions of distal buccal sides are parallel to each other, and frictional contact portions of mesial buccal sides are parallel to each other, and frictional contact portions of distal lingual sides are parallel to each other, and frictional contact portions of mesial lingual sides are parallel to each other.

5. The artificial molar teeth according to claim 4, wherein said frictional contact portions of the mesial lingual side of each said cusp of said maxillary molar teeth and said frictional contact portions of the distal buccal side of each said cusp of said mandibular molar teeth are parallel to each other, said frictional contact portions of the distal buccal side of each said cusp of said maxillary molar teeth and said frictional contact portions of the mesial lingual side of each said cusp of the mandibular molar teeth are parallel to each other, said frictional contact portions of the distal lingual side of each said cusp of said maxillary molar teeth and said frictional contact portions of the mesial buccal side of each said cusp of said mandibular molar teeth are parallel to each other, and said frictional contact portions of said mesial buccal side of each said cusp of said maxillary molar teeth and said frictional contact portions of the distal lingual side of each said cusp of said mandibular molar teeth are parallel to each other.

6. The artificial molar teeth according to claim 1, wherein cusp tops of adjacent teeth are disposed so as to coincide with each other.

7. The artificial molar teeth according to claim 2, wherein said two or more teeth includes mutually occluding teeth on opposed bases, and mutually parallel flat frictional contact portions are provided around mutually contacting cusps of two or more teeth.

8. The artificial molar teeth according to claim 2, wherein cusp tops of adjacent teeth are disposed so as to coincide with each other.

9. The artificial molar teeth according to claim 3, wherein cusp tops of adjacent teeth are disposed so as to coincide with each other.

10. The artificial molar teeth according to claim 4, wherein cusp tops of adjacent teeth are disposed so as to coincide with each other.

11. The artificial molar teeth according to claim 5, wherein cusp tops of adjacent teeth are disposed so as to coincide with each other.

12. The artificial molar teeth according to claim 2, wherein a bottom end of a fossa on said occlusal surface of said at least one tooth and said contact point are formed on a plane parallel to the mesial distal direction.

13. Artificial molar teeth comprising:

a base for being mounted in an oral cavity as a dental prosthetic appliance;

two artificial molar teeth arranged on the base and contacting each other at a contact point, at least one of the artificial molar teeth including an occlusal surface having cusps and a side groove, said occlusal surface further having an outer circumference defined by a ridge line extending over said cusps and crossing said side groove, said side groove extending toward a buccal side or lingual side, wherein said side groove extends from a fossa to a highest point of said side groove, wherein said side groove includes an intersecting point that intersects with said outer circumference of the occlusal surface, said intersecting point being located at the highest point of said side groove on said occlusal surface, and wherein said intersecting point and said contact point are arranged on a plane parallel to the mesial distal direction.

14. The artificial molar teeth of claim 13, wherein both of the two artificial molar teeth include an occlusal surface having cusps and a side groove, each of said occlusal surfaces further having an outer circumference defined by a ridge line extending over said cusps and crossing said side groove, said each of said side grooves extending toward a buccal side or lingual side, wherein each of said side groove extends from a fossa of the respective molar tooth to a highest point of said side groove, wherein each of said side grooves includes an intersecting point that intersects with said outer circumference of the occlusal surface of the respective molar tooth, said intersecting point being located at the highest point of said side groove on said occlusal surface, and wherein said intersecting points and said contact point are arranged on a plane parallel to the mesial distal direction.

* * * * *